United States Patent [19]

Medwid et al.

[11] Patent Number: 4,808,586

[45] Date of Patent: Feb. 28, 1989

[54] SUBSTITUTED BENZIMIDAZOLES AND BENZOTHIDIAZOLES HAVING ANTI-ASTHMATIC AND/OR ANTI-INFLAMMATORY ACTIVITIES

[75] Inventors: Jeffrey B. Medwid, Rockland County; Lawrence W. Torley, Orange County, both of N.Y.

[73] Assignee: American Cyanamid Company, Stamford, Conn.

[21] Appl. No.: 124,536

[22] Filed: Nov. 23, 1987

[51] Int. Cl.$^4$ .................. A61K 31/495; A61K 31/41; C07D 417/04; C07D 235/10
[52] U.S. Cl. ..................... 514/254; 514/394; 544/295; 544/357; 544/360; 544/368; 548/334
[58] Field of Search ............... 544/368, 357, 360, 295; 548/334; 514/254, 394

[56] References Cited

U.S. PATENT DOCUMENTS 3,192,108  6/1965  Brown et al. .................. 548/334
3,624,100  11/1971  Baselland et al. .................. 548/334
4,686,220  8/1987  Medwid et al. .................. 540/607

FOREIGN PATENT DOCUMENTS 1522040  4/1968  France .................. 548/334
982081  2/1965  United Kingdom .................. 548/334
1191112  5/1970  United Kingdom .................. 548/334

OTHER PUBLICATIONS

Zakhs et al, Chemical Abst. 65—15365g (1966).
Beznglyi et al., Chemical Abst., vol. 65, 15207h (1966).

*Primary Examiner*—Donald G. Daus
*Assistant Examiner*—Cecilia Shen
*Attorney, Agent, or Firm*—Edward A. Conroy, Jr.

[57]     ABSTRACT

This disclosure describes novel substituted 2-phenyl-1H-benzimidazoles and 2-phenyl-1H-benzimidazole-4,7-diones and novel 5-chloro-6-(4-substituted-1-piperazinyl)-2,1,3-benzothiadiazole-4,7-diones; all of which are highly active as anti-asthmatic and anti-allergic agents.

9 Claims, No Drawings

SUBSTITUTED BENZIMIDAZOLES AND BENZOTHIDIAZOLES HAVING ANTI-ASTHMATIC AND/OR ANTI-INFLAMMATORY ACTIVITIES

BRIEF SUMMARY OF THE INVENTION

This invention relates to new organic compounds and, more particularly, is concerned with novel substituted benzimidazoles (I), benzimidazole-4,7-diones (II), and benzothiadiazole-4,7-diones (III) which may be represented by the following structural formulae:

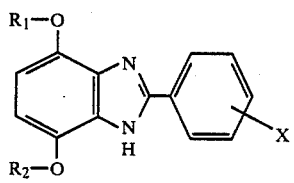
(I)

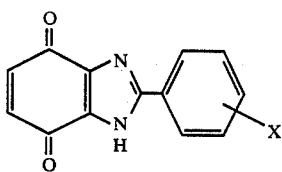
(II)

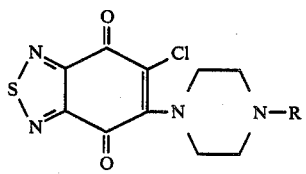
(III)

wherein $R_1$ and $R_2$ are the same and are hydrogen or alkyl ($C_1$–$C_3$); X is hydrogen, halogen (F, Cl, Br) or m-trifluoromethyl; and R is alkyl ($C_1$–$C_3$), alkanoyl($C_1$–$C_3$), carboalkoxy ($C_2$–$C_4$), phenyl, m-trifluoromethylphenyl, benzyl, 2-pyridyl, 2-pyrimidyl, 2-benzoxazolyl or 2-benzothiazolyl.

The organic bases of this invention form non-toxic acid-addition salts with a variety of pharmacologically acceptable organic and inorganic salt-forming reagents. Thus, acid-addition salts, formed by admixture of the organic free base with one or more equivalents of an acid, suitably in a neutral solvent, are formed with such acids as sulfuric, phosphoric, hydrochloric, hydrobromic, maleic, sulfamic, citric, lactic, malic, succinic, tartaric, acetic, benzoic, fumaric, gluconic, ascorbic, and the like. For purposes of this invention the free bases are equivalent to their non-toxic acid-addition salts. The acid-addition salts of the organic bases of the present invention are, in general, crystalline solids, relatively solube in water, methanol and ethanol but relatively insoluble in non-polar organic solvents such as diethyl ether, benzene, toluene, and the like.

This invention is also concerned with a method of treating asthma, allergic diseases, and inflammation in mammals by the administration of the novel compounds of the present invention, and with compositions of matter containing these compounds.

DETAILED DESCRIPTION OF THE INVENTION

The novel benzimidazole derivatives of the present invention may be readily prepared as set forth in the following reaction scheme wherein alkyl is ($C_1$–$C_3$) and X is as hereinbefore defined.

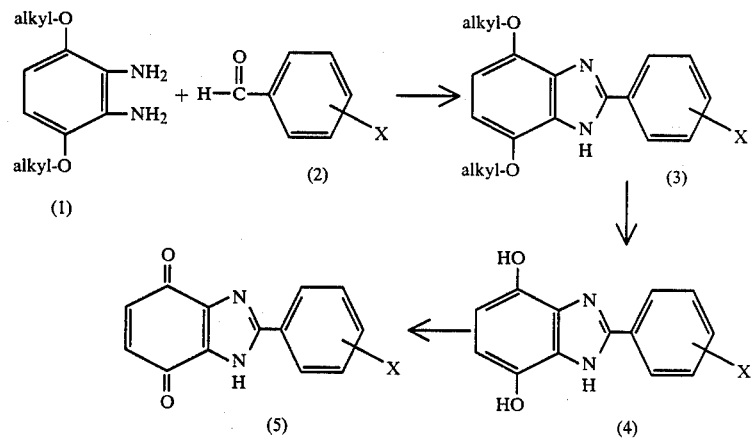

In accordance with the above reaction scheme, a 1,4-dialkoxy-2,3-diaminobenzene (1) is condensed with an appropriately substituted benzaldehyde (2) in a lower alkanol solvent at ambient temperatures to provide the corresponding 2-(substituted-phenyl)-4,7-dialkoxy-1H-benzimidazole (3). The conversion of (3) to (4) is best carried out with aluminum chloride in an inert solvent such as benzene, toluene or xylene at the reflux temperature for a few hours. The oxidation of (4) to (5) may be accomplished with a mixture of soldium sulfate and silver oxide in an inert solvent such as dimethylformamide, dioxane or tetrahydrofuran at ambient temperatures for a period of 10–15 hours.

The novel benzothiadiazole-4,7-dione derivatives of the present invention may be readily prepared by the reaction of 5-chloro-2,1,3-benzothiadiazole-4,7-dione with an N-monosubstituted piperazine of the formula:

wherein R is as hereinbefore defined. This reaction is preferably carried out in a lower alkanol solvent at reflux temperature for a few hours or in an inert solvent such as dioxane at ambient temperatures overnight.

The novel compounds of the present invention are highly active as antiasthmatic and antiallergic agents as will be demonstrated hereinbelow.

The bronchospasm of allergic asthma is a consequence of the release of mediators, such as histamine and slow-reacting substances from mast cells. The role of mediator release in the induction of an asthmatic attack has been fully reviewed and documented, see Kaliner, M. and Austen, K. F., Bronchial Asthama Mechanisms and Therapeutics, E. B. Weiss, Editor, Little, Brown and Company, Boston, 163 (1976); Lichtenstein, L. M., Asthma-physiology, Immunopharmacology and Treatment, Second International Symposium, L. M. Lichtenstein and K. F. Austen, Editors, Academic Press, New York, 51 (1979); and Bell, S. C., et al., Annual Reports in Medicinal Chemistry, 14, 51, H. J. Hess, Editor, Academic Press, New York (1979).

The novel compounds of this invention have been tested by the procedure of Lichtenstein, L. M. and Osler, A. G., J. Exp. Med., 120, 507–530 (1964), which evaluates the ability of compounds to inhibit mediator (histamine) release from immunologically stimulated human basophils.

REAGENTS

10X Concentrated Tris Buffer

Dissolve 140.3 g of sodium chloride, 7.45 g of potassium chloride and 74.5 g of Trizma-Tris Pre-Set, Reagent Grade, pH 7.6, at 25° C. (Sigma Chemical Co.) in sufficient water to give a final volume of 2 liters.

Human Albumin (Sigma Chemical Co.) (30 mg/ml)

Calcium and Magnesium Stocks

Made to 0.75M and 0.5M respectively, with calcium chloride dihydrate and magnesium chloride hexahydrate.

Tris-A Buffer

A 10 ml portion of 10X Tris Buffer and 1.0 ml of human albumin are diluted to 100 ml with water.

Tris ACM Buffer

A 10 ml portion of 10X Tris Buffer, 1.0 ml of human albumin, 0.8 ml of calcium stock and 0.2 ml of magnesium stock are diluted to 100 ml with water.

Rabbit Antihuman IgE

Behring Diagnostics (Generally used at 10 μg protein/ml final concentration).

House Dust Mite Extract (Dermatophagoides Farinae)

Strength 1:100 (w:v) allergenic extract, Hollister-Stier Labs. Generally this is diluted 1:1000 to 1:10,000 (considering the vial as stock).

Other Allergens

Intradermal solutions or intramuscular preparations for hyposensitization, Hollister-Stier Labs. The final concentration used is on the order of 1 PNU/ml.

Separation of Leukocytes from Human Blood and Challenge

Eighty milliliters of blood is withdrawn from subjects with known histamine release to anti-Ige, ragweed antigen or other specific alergen, using four 20 ml heparainized tubes. This 80 ml of blood is mixed with 20 ml of saline containing 0.6 g of dextrose and 1.2 g of dextran. The blood is allowed to sediment at room temperature in two 50 ml polycarbonate centrifuge tubes until a sharp interface develops between the red cells and plasma (60–90 minutes). The plasma (top) layer from each tube is with-drawn by pipet and transferred to respective 50 ml polycarbonate tubes. The plasma is centrifuged for 8 minutes at $100 \times G$ at 40° C. The supernatant is carefully poured off as completely as possible and the cell button is resuspended in 2–3 ml of Tris-A buffer using a silconized Pasteur pipet. The resuspension is accomplished by drawing the liquid gently in an out of the pipet, with the tip below the liquid, until and even suspension of cells is obtained. Sufficient Tris-A buffer is then added to bring the volume in the tube to about 45 ml and the tube is centrifuged at $110 \times G$ for 8 minutes at 4° C. The supernatant is poured off and the cell button is resuspended and centrifuged as described above. The supernatant is poured off and the cell button suspended in 2–3 ml of Tris-ACM buffer to make the final volume sufficient to allow addition to the reaction tubes.

Reaction tubes containing anti-IgE or antigens, either alone or with test compound in a total volume of 0.2 ml are prepared and placed in a 37° C. bath. The cells are warmed to 37° and frequently swirled to ensure an even suspension, while 1.0 ml aliquots are added to each reaction tube. The tubes are then incubated for 60 minutes at 37° C., vortexing the tubes gently every 15 minutes to keep the cells evenly suspended. When the reaction is complete, the tubes are centrifuged at 4° C. for 10 minutes at 1500 rpm to sediment the cells. One ml aliquots of supernatant are transferred to 12 mm by 75 mm polyethylene tubes and 0.2 ml of 8% perchloric acid is added to each tube. Blanks and totals are included in each test. The blanks have cells and all reagents except antigen or anti-IgE. The totals contain 0.24 ml of 8% perchloric acid, one ml of cells and 0.2 ml of buffer. All samples are then centrifuged to remove the precipitate protein.

Assay of Release Histamine by the Automated Fluormetric Method

This automated method has been described by Siraganian, R. P., in Anal. Biochem., 57 383 (1974) and J. Immunol. Methods, 7 283 (1975) and is based on the manual method of Shore, P. A., et al., J. Pharmacol. Exp. Ther., 217, 182 (1959).

The automated system consists of the following Technicon Autoanalyzer II components: Sampler IV, Dual-Speed Proportioning Pump III, Fluoronephelometer with a narrow pass primary filter 7-60 and a secondary filter 3-74, Recorder, and Digital Printer. The manifold used is the one described by Siraganian vide supra, with the following modifications: the dialyzer is omitted; all pumping tubes pass through a single proportioning pump with large capacity and twice the volume of sample is taken for analysis.

The automated chemistry consists of the following steps: Extraction from alkaline saline into butanol, back extraction into dilute hydrochloric acid by addition of heptane, reaction of histamine with o-phthaldialdehyde (OPT) at high pH and conversion of the OPT adduct to a stable fluorophore with phosphoric acid. The reaction product is then passed through the fluorometer. The full scale response is adjusted to 50 ng histamine base with a threshold sensitivity of approximately 0.5 ng.

Calculation of the Results of Histamine Release Tests

The instrument blank (wash) is substracted from the ng histamine of each sample. Then the ng histamine of each sample is divided by the mean of the three totals (cells lysed with perchloric acid) to obtain percent release.

Control samples contain antigen but no test compound. Blank (or spontaneous release) samples contain neither antigen nor test compound. The mean of the blanks (three replicates) is substracted from the percent release for controls and test compounds.

The means for control and tests compound groups are computed and the results for a test compound is computed as percent of control by the formula:

$$100 \cdot \times \frac{\% \text{ Histamine Release with Test Compound}}{\% \text{ Histamine Release in Controls}}$$

Values obtained at different concentrations of test compound are used to calculate and $ED_{50}$ (the concentration in $\mu M$ which causes a 50% inhibition of histamine release) by linear regression. A compound is considered active if the $ED_{50}$ is $\leq 48$ $\mu M$.

The results of this test on typical compounds of this invention appear in Table I.

TABLE I
Inhibition of Histamine Release from Immunologically Stimulated Human Basophils

| Compound | $ED_{50}$ $\mu M$ |
|---|---|
| 4-(6-Chloro-4,7-dihydro-4,7-dioxo-2,1,3-benzothiadiazol-5-yl)-1-piperazinecarboxylic acid, ethyl ester | 1.0 |
| 2-(4-Chlorophenyl)-1H—benzimidazole-4,7-diol | 9.7 |
| 2-(4-Chlorophenyl)-1H—benzimidazole-4,7-dione | 6.8 |
| 2-Phenyl-1H—benzimidazole-4,7-diol | 7.5 |
| 5-Chloro-6-[4-[3-(trifluoromethyl)-phenyl]-1-piperazinyl]-2,1,3-benzothiadiazole-4,7-dione | 9.1 |

The ability of these compounds to inhibit lipoxygenase activity in terms of the suppression of the release and biosynthesis of leukotriene B4 (LTB4) and 5-hydroxyeicosatetraenoic acid (5-HETE) was measured as follows.

In this assay $3 \times 10^7$ peritoneal neutrophils derived from guinea pigs were incubated at 37° C. in Dulbeccos buffer containing 50 mM tris buffer (pH 7.4). Five minutes before the addition of 100 $\mu M$ arachidonic acid and 20 $\mu M$ calcium ionophore (A23187), control vehicle or the test compounds were added to the neutrophils at a concentration of 10 $\mu g/ml$.

Three minutes after the addition of arachidonic acid and calcium ionophore the total lipid was partitioned into chloroform after adjusting the pH to 3 with citric acid and the addition of equal parts of methanol and chloro-form.

The 5-HETE and LTB4 were resolved by HPLC using a 5 $\mu M$, $4 \times 25$ cm octadecyl silica column (IBM Instruments) with 70–80% methanol in water adjusted to pH 3.0 with acetic acid. As the mobile phase was pumped at 1.0 ml/minute, LTB4 and 5-HETE were detected by absorbance at 270 and 236 nm, respectively.

LTB4 and 5-HETE were quantitated by comparison with the control and results were expressed as a percent of control. The lower the percentage, the more active the compound.

The results of this test on representative compounds of the invention appear in Table II.

TABLE II
Inhibition of Neutrophil Lipoxygenase from Immunoligically Stimulated Guinea Pig Neutrophiles

| Compound | % of Control | |
|---|---|---|
| | LTB4 | 5-HETE |
| 4-(6-(Chloro-4,7-dihydro-4,7-dioxo-2,1,3-benzothiadiazol-5-yl)-1-piperazinecarboxylic acid, ethyl ester | 39.3 | 40.5 |
| 2-(4-Chlorophenyl)-4,7-dimethoxy-1H—benzimidazole | 87 | 77 |
| 2-(4-Chlorophenyl)-1H—benzimidazole-4,7-dione | 0 | 4.3 |
| 2-(4-Chlorophenyl)-1H—benzimidazole-4,7-dione | 14.9 | 10.9 |
| 4,7-Dimethoxy-2-phenyl-1H—benzimidazole | 8 | 78.2 |
| 2-Phenyl-1H—benzimidazole-4,7-diol | 33.9 | 32.1 |
| 5-Chloro-6-[4-[3-(trifluoromethyl)-phenyl]-1-piperazinyl]-2,1,3-benzothiadiazole-4,7-dione | 14.6 | 15.2 |
| 5-[4-(2-Benzoxazolyl)-1-piperazinyl]-6-chloro-2,1,3-benzothiadiazole-4,7-dione | 25.8 | 20.8 |
| 4-(6-Chloro-4,7-dihydro-4,7-dioxo-2,1,3-benzothiadiazol-5-yl)-1-piperazinecarboxaldehyde | 90.8 | 64 |

The novel compounds of the present invention are effective as antiasthmatic agents in mammals when administered in amounts ranging from about 0.1 mg to about 100 mg/kg of body weight per day. A preferred dosage regimen for optimum results would be from about 0.1 mg to about 25 mg/kg of body weight per day, and such dosage units are employed that total of from about 7 mg to about 1.8 g of the active compound for a subject of about 70 kg of body weight are administered in a 24 hour period. This dosage regimen may be adjusted to provide the optimum therapeutic response. For example, serveral divided doses may be administered daily or the dose may be proportionally reduced as indicated by the exigencies of the therapeutic situation. A decided practical advantage is that these active compounds may be administered in any convenient manner such as by the oral, aerosol, intravenous, intramuscular, or subcutaneous routes.

The active compounds may be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions of preparations according to the present invention are prepared so that an oral dosage unit form contains between about 5 and 200 mg of active compound.

The tablets, troches, pills, capsules and the like may also contain the following: A binder such as gum tragacanth, acacia, corn starch or geleation; excipients such as dicalcium phosphate; a disintegrating agent such as corn starch, potato starch, alginic and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweentening agent, methyl and propyparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may contain various preservatives which may be used to prevent bacterial and fungal contamination. Such preservative are, for example, myristyl-gamma-picolinium chloride, benzalkonium chloride, phenethyl alcohol, p-chlorophenyl-alpha-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed. These compounds may also be administered by inhalation using conventional Aerosol(R) formulations.

The invention will be described in greater detail in conjunction with the following specific examples.

EXAMPLE 1

5-Chloro-2,1,3-benzothiadzole-4,7-dione

A mixture of 1.68 g of 5-chloro-2,1,3-benzothiadiazole-4,7-diol, 5.0 g of silver iodide, 2.0 g of anhydrous sodium sulfate and 100 ml of dioxane was stirred overnight, then heated at reflux for 2 hours, cooled and filtered. The filter cake was washed with dichloromethane, the filtrate and wash combined and concentrated in vacuo. The residue was crystallized from carbon tetrachloride, giving 1.1 g of the desired compound, mp 157.5°–158° C.

EXAMPLE 2

4-(6-Chloro-4,7-dihydro-4,7-dioxo-2,1,3-benzothiadiazol-5-yl)-1-piperazinecarboxylic acid, ethyl ester A solution of 332 mg of 1-piperazinecarboxylic acid, ethyl ester and 200.6 mg of 5-chloro-2,1,3-benzothiadiazole-4,7-dione in absolute ethanol was heated at reflux, with stirring. The mixture was then stirred for 2 hours at room temperature, evaporated, chromatographed on silica gel, eluting with chloroform and concentrated to a red oil. This oil was crystallized from dichloromethanehexane, giving 50 mg of the desired product, mp 152°–154° C.

EXAMPLE 3

2-(4-Chlorophenyl)-4,7-dimethoxy-1H-benzimidazole

A 19 g portion of 1,4-dimethoxy-2,3-dinitrobenzene in 200 ml of ethanol containing 1.0 g of platinum oxide was hydrogenated in a Parr apparatus. The mixture was filtered and to the filtrate was added 11.7 g of 4-chlorobenzaldehyde. The mixture was stirred overnight and the resulting solid collected. This solid was recrystallized from 200 ml of hot dimethylformamide, giving 10.13 g of the desired product, mp 274°–276° C.

EXAMPLE 4

2-(4-Chlorophenyl)-1H-benzimidazole-4,7-diol

A 1.0 g portion of 2-(4-chlorophenyl)-4,7-dimethoxy-1H-benzimidazole, 1.40 g of aluminum chloride and 50 ml of toluene was heated at reflux for 2 hours, then cooled and poured into cold 3N hydrochloric acid. The resulting solid was collected and recrystallized from ethanol, giving 680 mg of the desired product, mp>300° C.

EXAMPLE 5

2-(4-Chlorophenyl)-1H-benzimidazole-4,7-dione

A mixture of 1.0 g of 2-(4-chlorophenyl)-1H-benzimidazole-4,7-diol, 4 g of sodium sulfate and 1.3 g of silver oxide was stirred in p-dioxane for 12 hours and then filtered. The filtrate was evaporated and the residue crystallized from ethanol, giving 200 mg of the desired product as an orange solid, mp 270°–272° C. (dec.).

EXAMPLE 6

4,7-Dimethoxy-2-phenyl-1H-benzimidazole

A 22.8 g portion of 1,4-dimethoxy-2,3-dinitrobenzene in 200 ml of absolute ethanol was reduced in a Parr apparatus over platinum oxide. The mixture was filtered through diatomaceous earth. The filtrate was treated with 10.6 g of benzaldehyde and stirred for 48 hours. Most of the solvent was removed in vacuo. On standing, the remainder produced crystals which were collected and washed with ethanol, giving 6.7 g of the desired product, mp 226°–227° C.

EXAMPLE 7

2-Phenyl-1H-benzimidazole-4,7-diol

A 2.54 g portion of 4,7-dimethoxy-2-phenyl-1H-benzimidazole and 3.96 g of aluminum chloride in 125 ml of toluene were refluxed for 2 hours, then cooled and poured over cold dilute hydrochloric acid in ice. This mixture was stirred 0.5 hour, then the solid was collected, washed with water and dried, giving 2.0 g of the desired product, mp>280° C. (dec.).

EXAMPLE 8

5-Chloro-6-6[4-[3-(trifluoromethyl)phenyl]-1-piperazinyl]-2,1,3-benzothiadiazole-4,7-dione A solution of 690 mg of 3-(trifluoromethyl)phenyl-1-piperazine in 10 ml of p-dioxane was added to a solution of 600 mg of 5-chloro-2,1,3-benzothiadiazole-4,7-dione in p-dioxane, stirred overnight and then evaporated. The residue was taken up in dichloromethane, filtered and the filtrate evaporated in vacuo. The residue was crystallized from dichloromethane-hexane, giving 600 mg of the desired product, mp>200° C. (dec.).

EXAMPLE 9

5-[4-(2-Benzoxazolyl)-1-piperazinyl]-6-chloro-2,1,3-benzothiadiazole-4,7-dione

A 609 mg portion of 4-(2-benzoxazolyl)-1-piperazine and 600 mg of 5-chloro-2,1,3-benzothiadiazole-4,7-dione were reacted as described in Example 8, giving 222 mg of the desired product, mp 233°–235° C.

EXAMPLE 10

4-(6-Chloro-4,7-dihydro-4,7-dioxo-2,1,3-benzothiadiazol-5-yl)-1-piperazinecarboxaldehyde A 600 mg portion of 6-chlor-2,1,3-benzothiadiazole-4,7-dione and 342 mg of 1-piperazinecarboxaldehyde were reacted as described in Example 8, giving 164 mg of the desired product, mp 191°–194°.

We claim:

1. A compound selected from the group consisting of those of the formula:

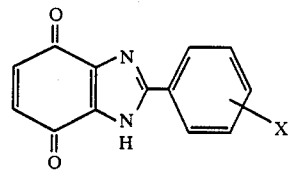

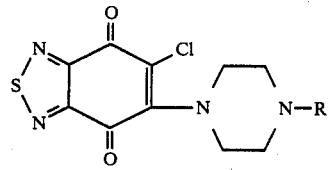

wherein X is hydrogen, fluoro, chloro, bromo or m-trifluoromethyl and R is alkanoyl($C_1$–$C_3$), carboalkoxy($C_2$–$C_4$), m-trifluoromethylphenyl or 2-benzoxazolyl and the pharmacologically acceptable acid-addition salts thereof.

2. The compound according to claim 1, formula (II) thereof; 4-(6-chloro-4,7-dihydro-4,7-dioxo-2,1,3-benzothiadiazol-5-yl)-1-piperazinecarboxylic acid, ethyl ester.

3. The compound according to claim 1, formula (I) thereof; 2-(4-chlorophenyl)-1H-benzimidazole-4,7-dione.

4. The compound according to claim 1, formula (II) thereof; 5-chloro-6-[4-[3-(trifluoromethyl)phenyl]-1-piperazinyl]-2,1,3-benzothiadiazole-4,7-dione.

5. The compound according to claim 1, formula (II) thereof; 5-[4-(2-benzoxazoly)-1-piperazinyl]-6-chloro-2,1,3-benzothiadiazole-4,7-dione.

6. The compound according to claim 1, formula (II) thereof; 4-(6-chloro-4,7-dihydro-4,7-dioxo-2,1,3-benzothiadiazol-5-yl)-1-piperazinecarboxaldehyde.

7. A method of treating asthma and allergic diseases in a mammal which comprises administering to said mammal an effective amount of a compound of claim 1.

8. An anti-asthmatic and/or anti-inflammatory composition of matter in dosage unit form comprising from about 5 mg to about 1500 mg of a compound of claim 1 in association with a pharmaceutically acceptable carrier.

9. A method of treating inflammation in a mammal which comprises administering to said mammal an effective amount of a compound of claim 1.

* * * * *